(12) United States Patent
Tomoike et al.

(10) Patent No.: US 6,515,196 B2
(45) Date of Patent: Feb. 4, 2003

(54) HEREDITARY POSTPRANDIAL HYPERTRIGLYCERIDEMIC RABBIT MODEL

(75) Inventors: Hitonobu Tomoike, Yamagata (JP); Kazuo Owada, Yamagata (JP); Tsunekata Ito, Yamagata (JP)

(73) Assignee: Yamagata University, Yamagata Pref. (JP)

( * ) Notice: Subject to any disclaimer, the term of this patent is extended or adjusted under 35 U.S.C. 154(b) by 0 days.

(21) Appl. No.: 09/725,050

(22) Filed: Nov. 29, 2000

(65) Prior Publication Data

US 2001/0027568 A1 Oct. 4, 2001

(30) Foreign Application Priority Data

Mar. 31, 2000 (JP) ........................................ 2000-097037

(51) Int. Cl.$^7$ ....................... A01K 67/00; A01K 67/033; A01K 67/027; C12N 15/00; G01N 33/00

(52) U.S. Cl. ................................ 800/9; 800/8; 800/14; 800/22; 800/3

(58) Field of Search ............................ 800/21, 3, 9, 14, 800/22, 8

(56) References Cited

PUBLICATIONS

Takasaki et al., A New Rabbit Strain with Heritable Hyper-colesterolemia and Hypertriglycerdemia, 1998, Lippoprotein Metab. Atherog., pp. 157–159.*

* cited by examiner

*Primary Examiner*—Scott D. Priebe
*Assistant Examiner*—Peter Paras, Jr.
(74) *Attorney, Agent, or Firm*—Burns, Doane, Swecker & Mathis, L.L.P.

(57) ABSTRACT

In attempts to determine the cause of hypertriglyceridemia, a model animal was established. This model is useful to analyze on the relationship between food ingestion and hypertriglyceridemia. When backcrossing of the Watanabe heritable hyperlipidemic rabbit and the Japanese white rabbit, individual rabbits with high triglyceride values were identified. A novel hereditary postprandial hypertriglyceridemic rabbit, characterized by normal serum triglyceride values under conditions of fasting and high levels of serum triglyceride value by ingestion of food was thus obtained.

8 Claims, 3 Drawing Sheets

HEREDITARY POSTPRANDIAL HYPERTRIGLYCERIDEMIC RABBIT MODEL

BACKGROUND OF THIS MODEL

1. Subject Matter

This model relates to a novel hereditary postprandial hypertriglyceridemia rabbit, with normal serum triglyceride values under conditions of fasting and high levels of serum triglyceride, postprandially 2. Description of the Related Art The three main causes of death worldwide are cancer, cardiac and cerebrovascular-related diseases. The number 1 cause of mortality in the United States is coronary heart disease. Accordingly, to limit the occurrence of vascular diseases is one of the most important medical challenges for the 21st century. The main underlying cause of vascular diseases is atherosclerosis. Factors closely related to the occurrence and severity of atherosclerosis have been elucidated in epidemiological studies and these factors are designated "risk factors". Known risk factors for atherosclerotic heart disease are hyperlipidemia, hypertension, diabetes, tobacco use and gender (male, menopausal females). Hyperlipidemia includes hypercholesterolemia, hypertriglyceridemia and a combination of these lipid abnormalities.

However, in the highly industrialized countries of Europe, North America and Japan, ingestion of higher nutrient food and excessive calories on a yearly increase. Consequently, hypertriglyceridemia have emerged as a serious risk factor in common diseases or even vascular-related diseases. Mechanisms governing hypertriglyceridemia and related cardiovascular diseases have yet to be fully elucidated. The relationship between food consumption and hypertriglyceridemia has to be clearly defined. Therefore, an animal model with postprandial hypertriglyceridemia has been investigated in hopes of throwing light on the problems

SUMMARY

The objective of this invention was to design an animal model with high levels of serum lipid following ingestion of food. Hyperlipidemia is a well accelerating factor for atherosclerosis. The effect of diet on lipid and lipoprotein concentration is well established. In clinical situations where hyperlipidemia is the main pathogenesis of atherosclerosis, postprandial hyperlipidemia has been considered a serious risk factor, which aggravates vascular diseases. However, whether postprandial hyperlipidemia is acquired or is heritable in nature, the characteristics of lipid metabolism in postprandial hyperlipidemia and how and when these lipid metabolisms aggregate have not investigated systematically. The model animal designed here will be used widely as a clinical specimen to explore these questions.

The Watanabe heritable hyperlipidemic rabbit (WHHL) has hyperlipidemia, and a pure line of rabbits with heritable combined hypercholesterolemia and hypertriglyceridemia after selected inbreedings was obtained and has been designated a hereditary hypertriglyceridemic rabbit (TGH: TG=triglyceride, H=high). Hypercholesterolemia in WHHL is caused by a genetic anomaly on LDL (low-density lipoprotein) receptor. The hereditary hypertriglyceridemia rabbit was selected from a WHHL rabbit sub-line, characterized by unusual high levels of triglyceride. The workers crossed TGH and Japanese White rabbit (JW) to determine the mode inheritance and individual rabbits with hypertriglyceridemia only after ingestion of food were identified. There have been no descriptions of a model animal with the hereditary trait of hypertriglyceridemia only after ingestion of food.

DETAILED DESCRIPTIONS

This invention concerns a hereditary postprandial hypertriglyceridemia rabbit with a level of serum triglyceride of 10 mg/dl to 200 mg/dl, under fasting conditions and a serum triglyceride value of 500 mg/dl to 3,000 mg/dl at 12~48 hours after ingestion of food. Hypertriglyceridemia means a triglyceride value of 500 mg/dl to 3,000 mg/dl, preferably 750 mg /dl to 2,500 mg/dl, and even more preferably 1,000 mg/dl to 2,000 mg/dl. The animal of this line exhibits hypertriglyceridemia only after ingestion of food; serum triglyceride levels are normal under fasting conditions. Moreover, in this hypertriglyceridemia persists for at least for 2 hours, from 12 hours to 48 hours after ingestion of food. Therefore this line is useful as a model animal of hypertriglyceridemia. This model animal has the autosomal dominant inheritance, and hypertriglyceridemia is particularly remarkable in males. Examinations of the triglyceride value were made on animals aged 3, 6, and 9 months. Manifestation of postprandial hypertriglyceridemia was observed after the age of 6 months.

The cholesterol value and the triglyceride value of the hereditary postprandial hypertriglyceridemia rabbit were 44±25 mg/dl and 113±60 mg/dl under conditions of fasting, respectively. On the other hand, after ingestion of food, the cholesterol and triglyceride levels were 118+50 mg/dl and 1,437±999 mg/dl, respectively. Therefore, the postprandial triglyceride levels increased markedly, 12 times over the fasting level. The hereditary hypertriglyceridemic rabbit did not exhibit any significant difference in life span, as compared with Japanese White rabbits (wild type). In addition, reproduction status was normal.

EXAMPLE (Measurements of Serum Lipids)

The value of serum lipid was measured as follows: Blood samples were collected from the ear vein of the rabbit and blood serum was separated by centrifuging for 15 minutes (4° C.) at 3,000 rpm. Measurements of cholesterol and triglyceride levels were made using a Vision Analyzer (Dinabot Co., Japan).

(Method for Production of a Hereditary Hypertriglyceridemia Rabbit)

The WHHL was distributed to the inventors in 1991 from Kyushu University through the courtesy of Dr. Yoshino WATANABE (Kobe University, School of Medicine). The inventors backcrossed this rabbit and Japanese White rabbit (JW), then attempted to establish the pure line (homozygote). The serum levels of cholesterol and triglyceride were measured, using enzymatic procedures. The results indicated that the levels of triglycerides in WHHL showed a broad distribution of 200 mg/dl to 900 mg/dl. On the other hand, the serum triglceride level in the Japanese White rabbit, which is genetically a wild type, was under 200 mg/dl and in most cases under 100 mg/dl.

Figure 1:
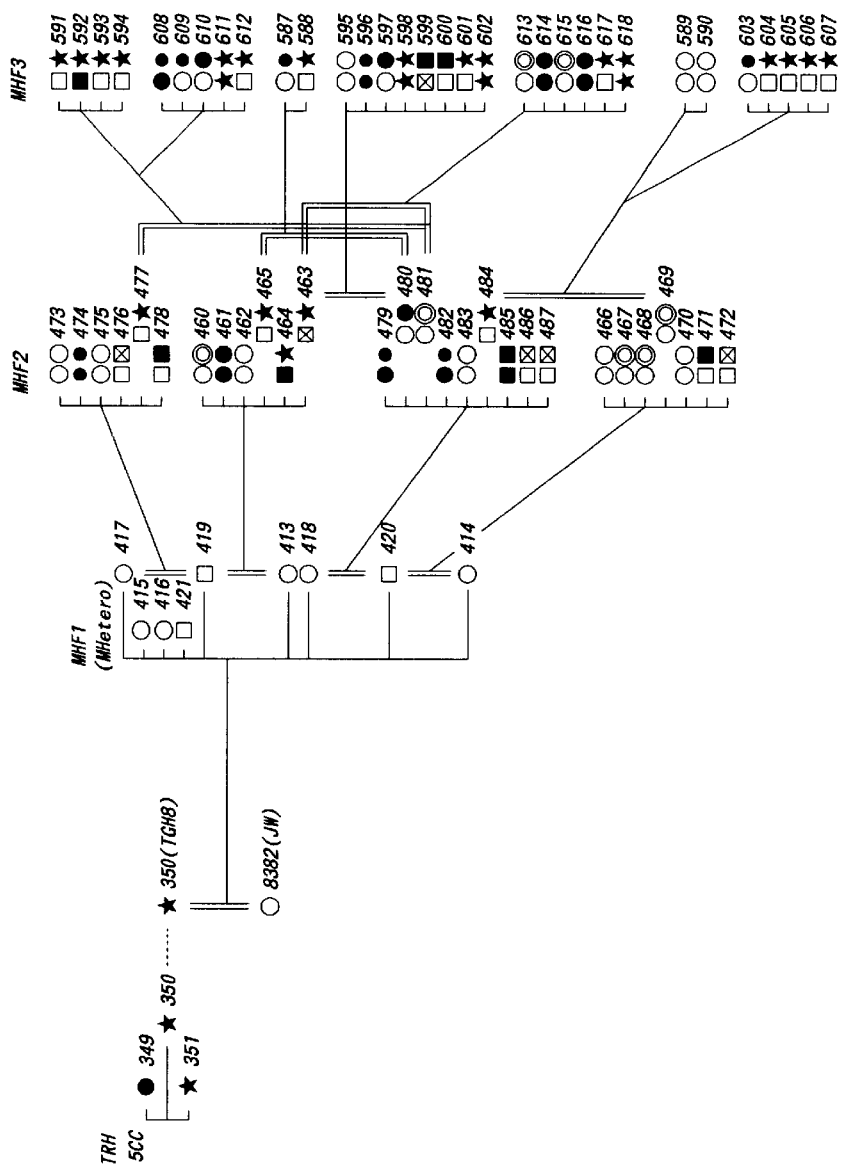
FIG. 1 is a family pedigree showing the process of crossing, in the acquisition of hereditary postprandial hypertriglyceridemia.
Figure 2:
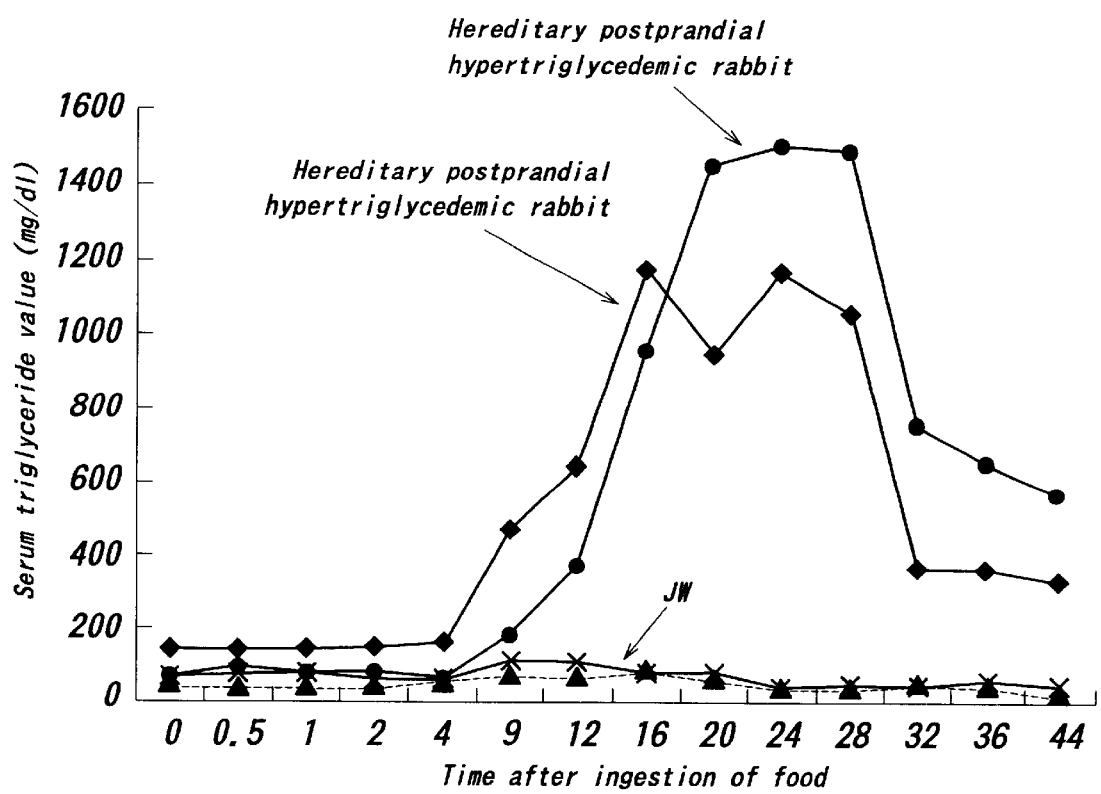
FIG. 2 is a graph showing the time course of serum triglyceride levels, after ingestion of food.

Next individual rabbits with high serum triglyceride values were crossed. As the result, the penetration rate of WHHL with a serum triglyceride level exceeding 500 mg/dl (TGH) increased with each generation. Namely, TGH appeared at a frequency of 90% at the 4th generation in 1995 and TGH appeared at a frequency of 100% after the fifth generation. As the result of analysis on the second generation (MHF2), produced by crossing within the first generation, the postprandial hypertriglyceridemia rabbits were evident among heterozygotes. Because crossings were of sibling crossing/heterozygotes, homozygotes of ¼, the hybrid of ¼, and the heterozygote of ⅔ are expected to be produced in the second generation, according to Mender's laws. Thus, the relation between food ingestion and serum lipid level of a rabbit with a unique characterization was recognized. This rabbit had serum triglyceride values exceeding 1,000 mg/dl 12 hours after ingestion of food, yet the lipid level was normal under conditions of fasting. Examination on genetic traits showed that postprandial hypertriglyceridemia was in the manner of autosomal dominant inheritance The family pedigree, showing the process of acquisition of the hereditary postprandial hypertriglyceridemia rabbit, is shown in FIG. 1. By backcrossing of WHHL and Japanese white rabbit, the backcross of first generation and (MHF 1) and the back-cross of second generation (MHF2) were produced. In MHF2, 7 individuals had characteristic of TGH and 26 individuals had normal lipid levels, Among these individuals, seven rabbits (male 4, female 3) with hypertriglyceridemia were crossed as seed animals. As a result, 32 rabbits (male 20, female 12) were obtained as the backcross third generation (MHF3). Nine individual rabbits had the characteristic of TGH, exhibiting serum hypertriglyceridemia, regardless of food ingestion. Twenty-three individuals exhibited hypertriglyceridemia after ingestion of a food, though the lipid level was normal under conditions of fasting. Therefore, it was confirmed that TGH is autosomal recessive, because the ratio of the individuals of TGH was about 25%. Moreover, as the number of individual rabbits with hypertriglyceridemia after ingestion of a food was 23, this characteristic seems to be inherited in a dominant inheritance manner, governed by a gene differing from that of TGH.

The relation between food ingestion and serum lipid levels was investigated using rabbits 3, 6, and 9 months old. No significant relationship between the amount of food ingested and the level of postprandial triglyceride was observed. Therefore, although postprandial hypertriglyceridemia is related to ingestion of food, it does not define lipid concentration in blood. The total cholesterol value in serum was compared under conditions of fasting and after food ingestion. As a result, a significant difference was not observed in rabbits at age 3 months. However, the serum total cholesterol value increased with ingestion of food, from 44 mg/dl to 118 mg/dl and from 41 mg/dl to 80 mg/dl, as average values, for animals of 6 months and for animals of 9 months, respectively. On the other hand, the serum triglyceride value was also compared under conditions of fasting and after food ingestion. The serum triglyceride value increased significantly with ingestion of a food, from 103 mg/dl to 236 mg/dl, from 113 mg/dl to 1,437 mg/dl and from 131 mgldl to 915 mg/dl, for animals ages, 3, 6 and 9 months, respectively. Concerning differences in gender, no difference was observed in serum triglyceride values under conditions of fasting. However, after ingestion of a food, the serum triglyceride levels of the males and females were 1,844 mg/dl and 675 mg/dl, respectively. The level of serum triglyceride observed in males was remarkably higher than in females.

Figure 3:
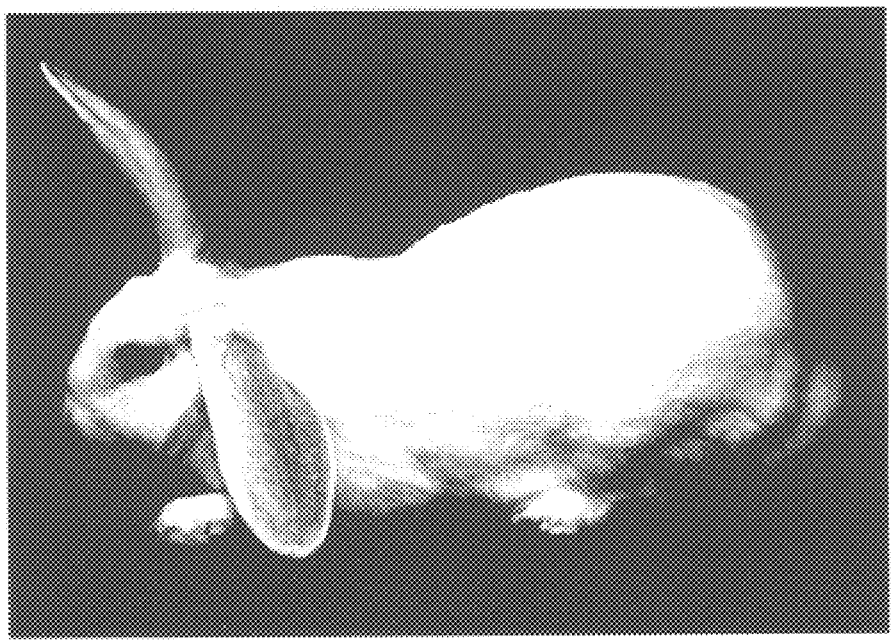
FIG. 3 is a photograph of a hereditary postprandial hypertriglyceridemia rabbit, as observed from the side.
Figure 4:
FIG. 4 is a photograph of hereditary postprandial hypertriglyceridemia rabbit, as observed from the front.

The time course of serum triglyceride values after ingestion of food was then observed. As shown in FIG. 3, when food was given to the rabbit after 24 hours of fasting, the serum triglyceride value increased rapidly from 8 hours. Serum triglyceride values reached the maximum, higher than 1,000 mg/dl, at 16–20 hours after ingestion of a food and this high level was maintained for 8–10 hours, then decreased. Such an extreme increase in serum triglyceride values was not observed in JW (Japanese White rabbit), which is a wild type. The photograph of the hereditary hypertriglyceridemia rabbit is shown in FIG. 3, as observed from the side and in FIG. 4 from the front.

(Breeding Conditions)

The laboratory animals were kept in the rabbit chamber in Yamagata University managed under breeding conditions, the temperature being 25° C. and the humidity 50–60%. Consistently, 120 g of solid food (Labo-R-Grower, Nihon Nosan Kogyo K.K., Tokyo) was provided daily. Tap water for drinking was freely available. On lighting, the chamber was illuminated from 6:00 a.m. to 6:00 p.m.

(Provider of the Animal Model)

The hereditary hypertriglyceridemia rabbit is provided as follows.

Storage and breeding: The Laboratory-Animal Center, Yamagata University, School of Medicine Preservation: Preserved as an individual animal.

The corresponding address: if required.

Zip Code: 990-9585

2-2-2 Iida-Nishi Yamagata City, Yamagata, JAPAN

First Department of Internal Medicine, Yamagata University, School of Medicine

Professor Hitonobu Tomoike

Telephone Number: 81-23-628-5302

Fax Number: 81-23-628-5305

The acquired model:

This hereditary postprandial hypertriglyceridemia rabbit has normal serum triglyceride values under conditions of fasting and high levels of serum triglyceride after ingestion of food.

Deposit Information:

Accession Number: FERM BP-7884

Date of Deposit: Feb. 8, 2002

Description of Deposit: Heterotype PHT (post-prandial hypertriglyeridemic) rabbit embryos. These embryos are obtained by first crossing the TGH rabbit with a Japanese White Rabbit. $F_1$ offspring are then crossed resulting in the PHT rabbit. The PHT rabbit is then crossed with a Japanese White Rabbit to obtain the deposited embryos.

Name/Address of Depository:
International Patent Organism Depository National Institute of Advanced Industrial Science and Technology
AIST Tsukuba Central 6, 1-1, Higashi 1-Chome Tsukuba shi, Ibaraki-ken 305-8566 JAPAN

What is claimed is:

1. A hereditary postprandial hypertriglyceridemia rabbit exhibiting serum triglyceride levels of 10 mg/dl to 200 mg/dl under conditions of fasting and serum triglyceride levels of 500 mg/dl to 3,000 mg/dl at a time point between 12 hours to 48 hours after ingestion of food, wherein the hereditary postprandial hypertriglyceridemia rabbit is a cross of a hereditary hypertriglyceridemic (TGH) rabbit with a Japanese White rabbit or is a descendent of a TGH/Japanese White rabbit crossing.

2. The rabbit according to claim 1, said serum triglyceride value being 750 mg/dl to 2,500 mg/dl at a time point between 12 hours to 48 hours after ingestion of food.

3. The rabbit according to claim 2, said serum triglyceride value being 1000 mg/dl to 2,000 mg/dl at a time point between 12 hours to 48 hours after ingestion of food.

4. The rabbit according to claim 1, wherein said postprandial hypertriglyceridemia is observed after age of 6 months.

5. The rabbit according to claim 1, wherein said postprandial hypertriglyceridemia is inherited in the manner of autosomal dominant inheritance.

6. The rabbit according to claim 1, wherein said rabbit is male.

7. The rabbit according to claim 1, wherein said rabbit is acquired by crossing with a TGH rabbit and a Japanese White rabbit.

8. The rabbit according to claim 1, exhibiting normal reproduction states.

* * * * *